United States Patent [19]

Goldstein et al.

[11] Patent Number: 5,411,518
[45] Date of Patent: May 2, 1995

[54] MEDICAL TOURNIQUET APPARATUS

[75] Inventors: Gary W. Goldstein, Everett; Jeffrey B. Tedeschi, Kirkland, all of Wash.

[73] Assignee: Design +3, Incorporated, Everett, Wash.

[21] Appl. No.: 248,186

[22] Filed: May 24, 1994

[51] Int. Cl.⁶ ............................................. A61B 17/00
[52] U.S. Cl. ................................. 606/202; 128/686
[58] Field of Search .............................. 606/201–203; 128/677–686; 602/75, 62

[56] References Cited

U.S. PATENT DOCUMENTS

| | | | |
|---|---|---|---|
| 3,171,410 | 3/1965 | Towle, Jr. et al. | 606/202 |
| 3,633,567 | 1/1972 | Sarnoff | 606/202 |
| 3,756,239 | 9/1973 | Smythe | 128/686 |
| 3,884,240 | 5/1975 | Gilman | 606/201 |
| 4,354,503 | 10/1982 | Golden . | |
| 4,605,010 | 8/1986 | McEwen . | |
| 4,616,644 | 10/1986 | Saferstein et al. . | |
| 4,635,635 | 1/1987 | Robinette-Lehman . | |
| 4,637,394 | 1/1987 | Racz et al. . | |
| 4,838,276 | 6/1989 | Nagai et al. . | |
| 4,869,265 | 11/1989 | McEwen . | |
| 4,979,953 | 12/1990 | Spence . | |
| 5,179,957 | 1/1993 | Williams . | |
| 5,193,549 | 3/1993 | Bellin et al. . | |
| 5,201,758 | 4/1993 | Glover . | |

FOREIGN PATENT DOCUMENTS

| | | | |
|---|---|---|---|
| 0240666 | 11/1986 | Denmark | 606/203 |
| 0290046 | 8/1935 | Italy | 606/202 |

Primary Examiner—Stephen C. Pellegrino
Assistant Examiner—William W. Lewis
Attorney, Agent, or Firm—Richard C. Litman

[57] ABSTRACT

The present invention is an apparatus for wrapping around a body member to restrict the flow of blood. This apparatus includes a tourniquet having an inflatable plenum, and a pad for minimizing patient discomfort. The pad is positionable between the tourniquet and the body member, and it is fabricated from a substantially absorbent, wrinkle free material. A stiffener positioned within the inflatable plenum assures that the tourniquet applies a uniform pressure upon the body member to which it is applied. The stiffener is partially shape retaining for holding the tourniquet in a circular configuration.

18 Claims, 4 Drawing Sheets

MEDICAL TOURNIQUET APPARATUS

BACKGROUND OF THE INVENTION

1. Field of the Invention

The present invention relates to a tourniquet apparatus for controlling the flow of blood through a body member. Specifically, the invention relates to a tourniquet apparatus that will not damage the skin to which it is applied and will exert a substantially uniform pressure thereto.

2. Description of the Prior Art

It is desired to produce a medical tourniquet that is inexpensive to manufacture, and is capable of supplying a uniform pressure upon the perimeter of the body member to which it is applied. Such a tourniquet should be reliable, and should not harm the skin of the patient, even if it is applied for an extended period of time.

Prior art tourniquets have been designed in a plurality of configurations. One common design in the prior art includes a semi-rigid element that is sufficiently flexible to bend with the rest of the tourniquet, but is sufficiently rigid to limit and standardize the radial distention of the air containing bladder or plenum. One patent showing the use of such a semi-rigid member is U.S. Pat. No. 4,979,953 issued to Jerry L. Spence on Dec. 25, 1990. The medical tourniquet of this invention includes an inflatable bladder formed from the welded attachment of two polymer impregnated, fabric wall members. A cover surrounds these wall members, and a stiffener plate is held inside the cover, but outside the bladder.

Other patents utilizing a semi-rigid element are U.S. Pat. No. 4,605,010 issued to James A. McEwen on Aug. 12, 1986; U.S. Pat. No. 4,635,635 issued to Cynthia Robinette-Lehman on Jan. 13, 1987; and U.S. Pat. No. 5,201,758 issued to Dennis Glover on Apr. 13, 1993. The McEwen patent discloses the use of a thermoplastic stiffener wrapped around a bladder, after the bladder has been secured to the patient's limb. This stiffener includes a plurality of holes for receiving pins protruding from the bladder. The mating of the pins and the stiffener removably secures the stiffener to the bladder.

The Robinette-Lehman patent discloses a tourniquet an inflatable bladder with a flexible, two piece exterior backing. A stiffener is positioned between the two pieces of the backing, which are sealed to secure the stiffener therebetween. The Glover patent illustrates an inflatable bladder positioned within a cavity formed between a backing plate and a flexible cover.

Common designs of prior art tourniquets include an air plenum formed from two facing surfaces fused together at their perimeters. U.S. Pat. No. 5,179,957 issued to Michael Williams on Jan. 19, 1993, illustrates a blood pressure cuff formed from a polyurethane nylon sheet folded upon itself. The facing edges of the sheet are fused together to form an inflatable bladder. Appropriate hook and loop fasteners are fused to the surface of the bladder, and are utilized for attaching the cuff to the patient's arm.

Other patents utilizing the technique of welding to secure facing walls of a bladder are U.S. Pat. No. 4,637,394 issued to Gabor B. Racz et al. on Jan. 20, 1987, and U.S. Pat. No. 5,193,549 issued to Matthew Bellin, et al. on Mar. 16, 1993. The Racz et al. patent illustrates a tourniquet having an interior chamber formed from an expansible elastomeric material. One method for securing the edges of this wall to each other is by heat welding. The Bellin et al. patent discloses a cuff having an inflatable compartment defined by a film material. This inflatable compartment is enclosed within a second compartment fabricated from the loop portion of hook and loop fabric. This loop portion is electromagnetically welded to the film material of the inflatable compartment, thus eliminating the need for both adhesives and for sewing.

None of the above inventions and patents, taken either singly or in combination, is seen to describe the instant invention as claimed.

SUMMARY OF THE INVENTION

The present invention is an easily manufactured apparatus for restricting flow of blood through a body member. This apparatus includes a tourniquet for circumferentially encircling the body member. The tourniquet is formed from a pair of flexible walls secured to each other to form an inflatable plenum therebetween. A substantially absorbent, wrinkle free pad is positionable between the tourniquet and the body member. This pad minimized the discomfort of the patient to which the tourniquet is applied.

In one embodiment of the invention, the tourniquet is disposable. In this embodiment, the flexible walls are fabricated from thermoplastic material impregnated with a fabric exterior. One of these fabric exteriors is a hook or loop type fastening material for mating with a strap attached to one end of the tourniquet. This strap engages, and secures to, the fastening material to hold the tourniquet around the body member. In a second embodiment of the invention, the flexible walls are fabricated from a cleanable vinyl material, and therefore, the tourniquet of this embodiment may be safely reused.

A stiffener positioned within the plenum is slightly smaller than the plenum interior, and therefore, it maintains the plenum in its intended shape. This assures that the tourniquet applies a uniform pressure upon the body member to which it is applied. The stiffener is partially shape retaining for holding the tourniquet in a circular configuration.

Accordingly, it is a principal object of the invention to provide an easily manufactured apparatus for restricting the flow of blood through a body member.

It is another object of the invention to provide a novel tourniquet apparatus that minimizes the discomfort of the patient to which the tourniquet is applied.

It is a further object of the invention to provide a novel tourniquet apparatus that supplies a substantially uniform pressure upon the perimeter of a body member.

Still another object of the invention is to provide a novel tourniquet apparatus that is easily applied to a body member.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
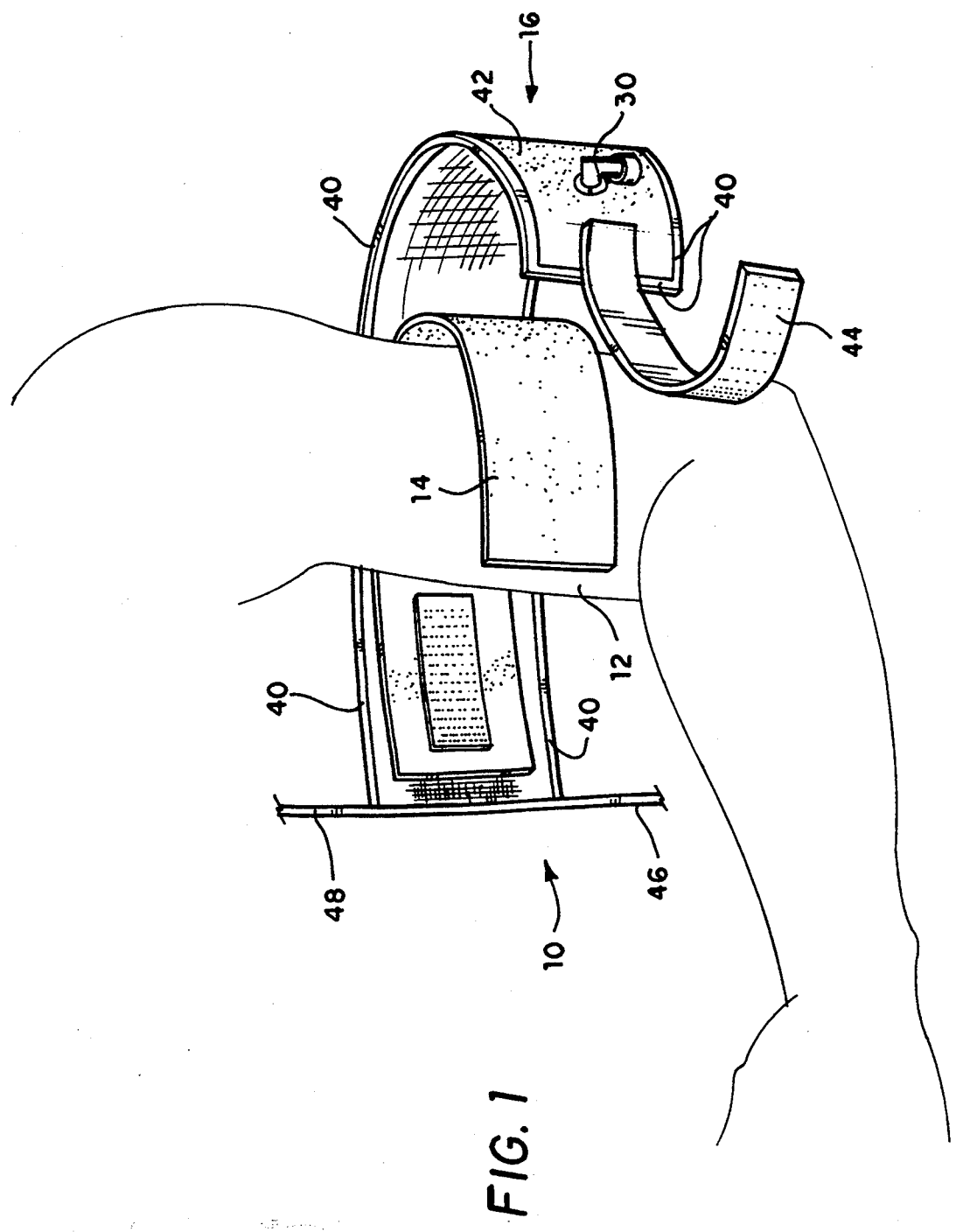
FIG. 1 is an environmental, partially exploded, perspective view of a first embodiment of the apparatus of the invention.

The present invention is an apparatus 10 for restricting the flow of blood through a body member. In FIG. 1, apparatus 10 is illustrated relative to a patient's biceps 12, which represents one body member to which apparatus 10 can be applied. The apparatus 10 includes a pad 14 and a disposable tourniquet 16, both of which circumferentially wrap around the biceps 12. Pad 14 is for minimizing patient discomfort, and it is wrapped directly around biceps 12. This pad 14 is substantially absorbent and substantially wrinkle free. The tourniquet 16 is wrapped around pad 14, and is capable of exerting a circumferential force upon pad 14, and therefore the area of biceps 12 underneath pad 14. This circumferential force restricts the flow of blood through biceps 12.

Figure 2:
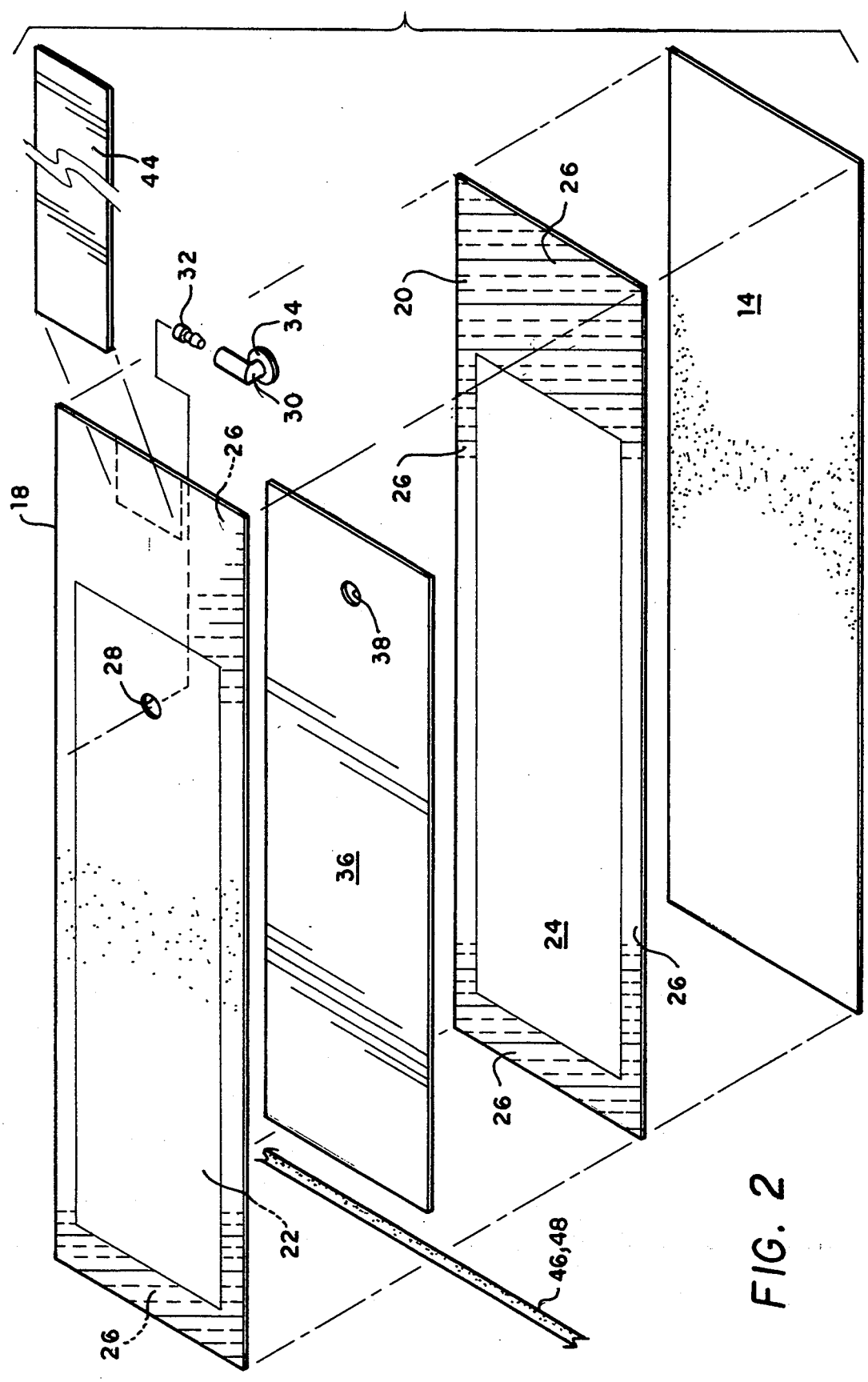
FIG. 2 is an exploded, perspective view of the apparatus shown in FIG. 1.

Referring primarily to FIG. 2, tourniquet 16 includes a first plenum wall 18 and a second plenum wall 20. These walls 18,20 are attached to each other to form a plenum bordered by the interior face 22 and the interior face 24. Although the preferred method for attaching walls 18,20 is to provide a radio frequency weld along the boundary 26, any appropriate sealing method could suffice.

First plenum wall 18 includes a port 28 for attachment thereto of a standard valve 30 and a standard connector, such as a luer connector 32. This luer connector 32 is for receiving a conventional air supply source to either force air into, or extract air from, the plenum. Luer connector 32 is welded to valve 30, and the flange 34 is welded to the portion of interior face 22 that defines port 28.

Located between walls 18,20 is a stiffener 36 fabricated from a partially shape retaining material. This stiffener 36 maintains tourniquet 16 in a circular configuration, which facilitates attachment of tourniquet 16 to body member 12. The dimensions of stiffener 36 correspond to, but are slightly less than, the dimensions of the plenum. Therefore, stiffener 36 prevents wrinkling and undesired bending or twisting of the flexible material of walls 18,20. This assures that tourniquet 16 applies a uniform pressure upon the circumference of pad 14.

When the plenum is inflated, air completely surrounds stiffener 36. However, as the dimensions of stiffener 36 are slightly less than the dimensions of the plenum, air flow is partially restricted around the perimeter of stiffener 36. To compensate for this restriction of air flow, stiffener 36 is fabricated to include at least one opening 38 for expediting the passage of air from one side of the stiffener to the other. When air is permitted to circulate freely to either side of stiffener 36, equal and opposite air forces are applied to stiffener 36. In this state of equilibrium, stiffener 36 is prevented from bowing, and the uniform distribution of pressure is maintained.

The configuration of stiffener 36 inside the plenum greatly reduces the manufacturing cost of tourniquet 16. Placement of stiffener 36 inside the plenum eliminates the need to have a separate containment device for stiffener 36. This reduces manufacturing cost by minimizing the amount of necessary materials. Also, the placement of stiffener 36 inside the plenum eliminates the need for adhesives, which often cause an escalation in the manufacturing cost of prior art tourniquets. As tourniquets are commonly disposed of after a single use, reducing the cost of a tourniquet is of utmost importance.

The preferred material for the walls 18, 20 is any flexible and weldable thermoplastic material, such as polyurethane. The exterior surface of the first plenum wall is impregnated with either a hook or loop fabric material, such as polyester. The exterior surface of the second plenum wall is impregnated with a fabric material, such as nylon, which is flexible and also comfortable to touch. Border 40 (FIG. 1) is secured upon the edges of the walls 18, 20 to prevent these edges from fraying.

The hook or loop material of the exterior surface 42 is capable of mating with the hook or loop material of the interior surface of the strap 44. Therefore, to secure the tourniquet upon a body member, the tourniquet is wrapped around the body member, and the strap 44 is secured to exterior surface 42. Tie straps 46, 48 extend around the tourniquet to provide further stabilization.

As mentioned above, pad 14 is for placement between the tourniquet and the body member. In the preferred embodiment, this pad is fabricated from a material that is approximately 92% viscous rayon and approximately 8% polypropylene. This combination of materials creates a pad that is substantially absorbent and is substantially wrinkle free.

The absorbent nature of the pad increases patient comfort by extracting fluids away from the skin. As the tourniquet is often attached to a body member for a substantial amount of time, this extracting of fluids is instrumental in removing perspiration that forms between the pad and the patient's skin. If not absorbed, this perspiration could create an unsanitary and uncomfortable environment.

The wrinkle free nature of the pad provides a smooth surface for engaging the patient's skin. If the surface that engages the skin is permitted to wrinkle so as to partially fold upon itself, such a wrinkle could excessively press against the patient's skin. Not only could this result in an extremely uncomfortable condition for the patient, but also it is likely to cause either temporary or permanent damage to the patient's skin.

The choice of materials for the pad allows the pad to be fabricated such that a plurality of either hook or loop fasteners are formed upon its face. As illustrated in FIG. 1, the end of the pad includes a strip of material having a plurality of either hook or loop fasteners that mate with, and secure to, the pad face. This arrangement allows the pad to be circumferentially wrapped around a body member, and then independently secured thereto by the engagement of the strip and the pad face.

That the pad is separate from the tourniquet permits the pad to be wrapped upon the body member without being influenced by the tourniquet. Therefore, if the tourniquet should crease upon being applied to the pad, it slides or floats relative to the pad, not altering the wrinkle free placement of the pad. If the pad is fabricated to be of a substantial length, it can be wrapped around the body member a multiple number of times. This multiple wrapping firmly secures the inner most wrap to the user's skin, further eliminating the likelihood that the pad will crease.

Figure 3:
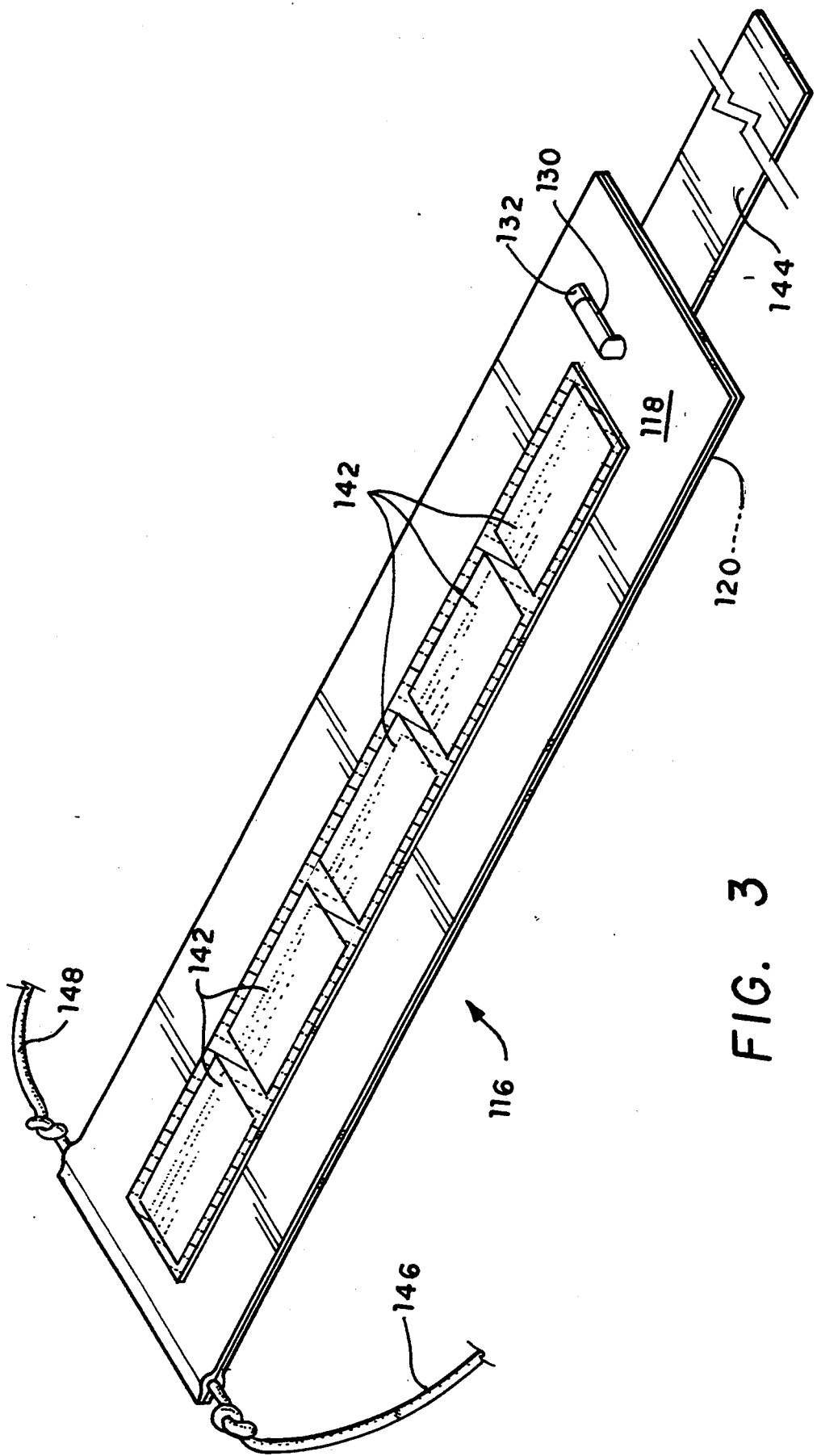
FIG. 3 is a perspective view of a second embodiment of the apparatus of the invention.

A second embodiment of the tourniquet is illustrated in FIG. 3, at 110. This arrangement of this tourniquet is equivalent to tourniquet 10, except for the materials utilized. In this embodiment, exterior surfaces 118, 120 are fabricated from a weldable, but steam cleanable material, such as vinyl. Additionally, the hook and loop fasteners 142, 144, the tie straps 146, 148, the standard valve 130, and the luer connector 132 are fabricated from a similar steam cleanable material. Therefore, the tourniquet can be re-used, if properly cleaned and sterilized.

Figure 4:
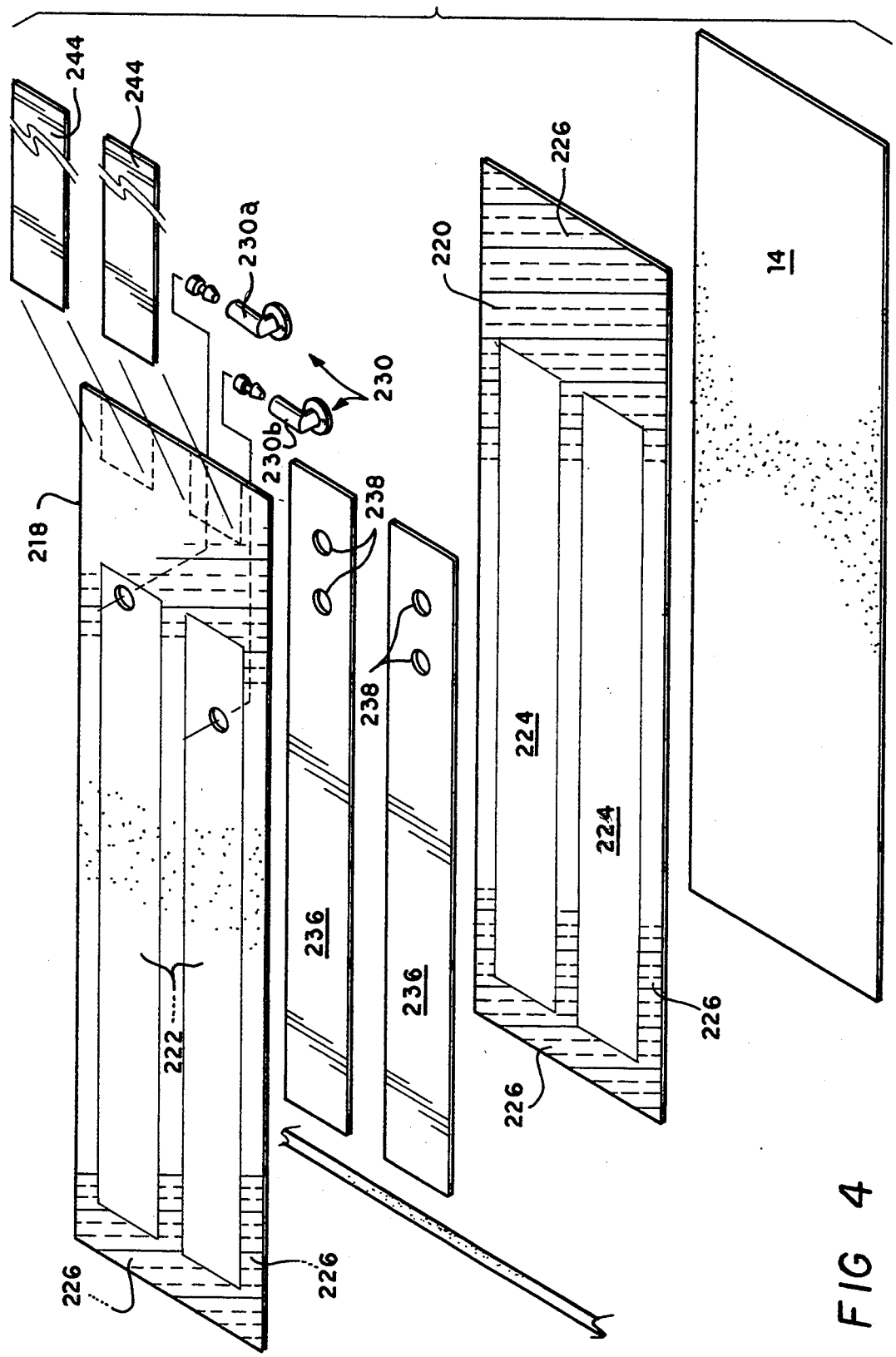
FIG. 4 is an exploded, perspective view of a third embodiment of the apparatus of the invention.

Still another embodiment of the tourniquet is illustrated in FIG. 4. This tourniquet is usable with pad 14, and it could be fabricated from the material of either tourniquet 16 or tourniquet 116. As depicted in the figures, this tourniquet includes a pair of plenums defined within faces 222,224, formed from the attachment of wall 218 to wall 220 at the boundary 226. Each of these plenums is independently inflated and deflated through the valves 230a, 230b, respectively.

As known in the tourniquet industry, this dual plenum arrangement permits the plenum most proximate to the patient's heart to be initially inflated. Before the distal plenum is inflated, anesthesia is injected into the part of the patient's body member on the side of the tourniquet remote from the patient's heart. After this anesthesia has taken affect, the distal plenum is inflated and the proximate plenum is deflated. The result is that the constriction forces of the tourniquet act upon a location of the patient that is numbed by the anesthesia.

As illustrated in FIG. 4, each plenum includes its own stiffener, 236, 236. These stiffeners are each shown to include two openings 238, 238, each of which allow for the passage of air therethrough. The configuration of a separate stiffener for each plenum assures the independence of each plenum. In configurations where one stiffener is to influence more than one plenum, true independence of the plenums is not achieved. In order to properly inflate or deflate each plenum to a specific pressure, full independence of the plenums must be achieved.

To facilitate attachment of air supply devices, valve 230a is slightly offset from valve 230b. Additionally, the use of two straps 244, 244 allows for differentiating the proximate side of the tourniquet from the distal side of the tourniquet. One strap 244 is a first color, and the other strap 244 is a second color.

It is to be understood that the present invention is not limited to the embodiments described above, but encompasses any and all embodiments within the scope of the following claims.

We claim:

1. An apparatus for restricting the flow of blood through a body member, said apparatus comprising a tourniquet for circumferentially encircling the body member, said tourniquet comprising:
   a first plenum wall having a first interior face;
   a second plenum wall having a second interior face;
   means for attaching said first plenum wall to said second plenum wall, thereby forming at least one enclosed plenum bordered by said first interior face and said second interior face;
   means for permitting the passage of fluid into and out from said at least one enclosed plenum;
   at least one stiffener positioned within said at least one enclosed plenum, wherein each of said at least one enclosed plenum includes therein only one of said at least one stiffener;
   a pad positionable between said tourniquet and said body member, said pad comprising a pad face and a pad end, said pad being fabricated from a substantially absorbent, wrinkle resistant material;
   means for removably attaching said pad end to said pad face, thereby allowing said pad to be independently and circumferentially secured upon said body member; and
   means for securing said tourniquet around said body part.

2. The apparatus according to claim 1, wherein said pad is fabricated from a pad material comprising approximately 92% viscous rayon and approximately 8% polypropylene.

3. The apparatus according to claim 2, wherein said pad material forms one of a plurality of hooks and a plurality of loops, there being a strip of material secured to said pad end, said strip of material configured to include one of a plurality of hooks and a plurality of loops for mating with said pad material.

4. The apparatus according to claim 1, wherein said at least one stiffener is configured to define at least one opening therethrough.

5. The apparatus according to claim 1, wherein said first plenum wall includes a first exterior surface, said first exterior surface being impregnated with one of a hook and loop fastener, said means for securing comprising a strap extending from said tourniquet, said strap configured to include one of a hook and loop fastener for mating with said first exterior surface.

6. The apparatus according to claim 1, wherein said at least one enclosed plenum is made up of two enclosed plenums, each of said two enclosed plenums having independent said means for permitting the passage of fluid into and out from said each of said two enclosed plenums.

7. An apparatus for restricting the flow of blood through a body member, said apparatus comprising a tourniquet for circumferentially encircling the body member, said tourniquet comprising:
   a first plenum wall having a first interior face;
   a second plenum wall having a second interior face;
   means for attaching said first plenum wall to said second plenum wall, thereby forming at least one enclosed plenum bordered by said first interior face and said second interior face;
   means for permitting the passage of fluid into, and out from, said at least one enclosed plenum;
   a pad positionable between said tourniquet and the body member, said pad fabricated from a substantially absorbent, wrinkle resistant material, said pad comprising a pad face and a pad end;
   means for removably attaching said pad end to said pad face, thereby allowing said pad to be independently, circumferentially secured upon the body member; and
   means for securing said tourniquet around the body part.

8. The apparatus according to claim 7, wherein said pad is fabricated from a pad material comprising approximately 92% viscous rayon and approximately 8% polypropylene.

9. The apparatus according to claim 7, wherein said pad material forms one of a plurality of hooks and a plurality of loops, there being a strip of material secured to said pad end, said strip of material configured to include one of a plurality of hooks and a plurality of loops for mating with said pad material.

10. The apparatus according to claim 7, further including at least one stiffener positioned within said at least one enclosed plenum, wherein each of said at least one enclosed plenum includes therein only one of said at least one stiffener.

11. The apparatus according to claim 7, wherein said at least one stiffener is configured to define at least one opening therethrough.

12. The apparatus according to claim 7, wherein said first plenum wall includes a first exterior surface, said first exterior surface being impregnated with one of a hook and loop fastener, said means for securing comprising a strap extending from said tourniquet, said strap configured to include one of a hook and loop fastener for mating with said first exterior surface.

13. The apparatus according to claim 7, wherein said at least one enclosed plenum is two enclosed plenums, each of said two enclosed plenums having independent said means for permitting the passage of fluid into and out from said each of said two enclosed plenums.

14. An apparatus for restricting the flow of blood through a body member, said apparatus comprising a tourniquet for circumferentially encircling the body member, said tourniquet comprising:

a first plenum wall having a first interior face;

a second plenum wall having a second interior face;

means for attaching said first plenum wall to said second plenum wall, thereby forming at least one enclosed plenum bordered by said first interior face and said second interior face;

means for permitting the passage of fluid into, and out from, said at least one enclosed plenum;

a pad having a pad face and a pad end, said pad being positionable between said tourniquet and the body member, said pad fabricated from a pad material comprising approximately 92% viscous rayon and approximately 8% polypropylene, said pad material being substantially absorbent, and substantially wrinkle resistant, said pad material being fabricated to include one of a plurality of hooks and a plurality of loops, there being a strip of material secured to said pad end, said strip of material configured to include one of a plurality of hooks and a plurality of loops for mating with said pad material;

means for removably attaching said pad end to said pad face, thereby allowing said pad to be independently, circumferentially secured upon the body member; and means for securing said tourniquet around the body part.

15. The apparatus according to claim 14, further including at least one stiffener positioned within said at least one enclosed plenum, wherein each of said at least one enclosed plenum includes therein only one of said at least one stiffener.

16. The apparatus according to claim 15, wherein said at least one stiffener is configured to define at least one opening therethrough.

17. The apparatus according to claim 14, wherein said first plenum wall includes a first exterior surface, said first exterior surface being impregnated with one of a hook and loop fastener, said means for securing comprising a strap extending from said tourniquet, said strap configured to include one of a hook and loop fastener for mating with said first exterior surface.

18. The apparatus according to claim 14, wherein said at least one enclosed plenum is two enclosed plenums, each of said two enclosed plenums having independent said means for permitting.

* * * * *